(12) United States Patent  
Dettinger et al.

(10) Patent No.: US 7,925,672 B2  
(45) Date of Patent: *Apr. 12, 2011

(54) METADATA MANAGEMENT FOR A DATA ABSTRACTION MODEL

(75) Inventors: Richard D. Dettinger, Rochester, MN (US); Daniel P. Kolz, Rochester, MN (US); Richard J. Stevens, Rochester, MN (US); Jeffrey W. Tenner, Rochester, MN (US); Shannon E. Wenzel, Colby, WI (US)

(73) Assignee: International Business Machines Corporation, Armonk, NY (US)

( * ) Notice: Subject to any disclaimer, the term of this patent is extended or adjusted under 35 U.S.C. 154(b) by 42 days.

This patent is subject to a terminal disclaimer.

(21) Appl. No.: 12/369,204

(22) Filed: Feb. 11, 2009

(65) Prior Publication Data

US 2009/0144251 A1 Jun. 4, 2009

Related U.S. Application Data

(63) Continuation of application No. 10/955,467, filed on Sep. 30, 2004, now Pat. No. 7,505,958.

(51) Int. Cl.  
*G06F 17/30* (2006.01)

(52) U.S. Cl. ........................................ 707/797; 707/802

(58) Field of Classification Search .................. None  
See application file for complete search history.

(56) References Cited

U.S. PATENT DOCUMENTS

| 5,692,184 | A | 11/1997 | Ardoin et al. |
| 6,725,227 | B1 | 4/2004 | Li |
| 6,760,721 | B1 | 7/2004 | Chasen et al. |
| 6,970,874 | B2 | 11/2005 | Egilsson et al. |
| 6,996,558 | B2 | 2/2006 | Dettinger et al. |
| 7,114,147 | B2 | 9/2006 | Ballantyne et al. |
| 7,124,364 | B2 | 10/2006 | Rust et al. |
| 7,143,388 | B1 * | 11/2006 | Miller et al. .................... 716/18 |
| 7,505,958 | B2 | 3/2009 | Dettinger et al. |
| 2003/0200522 | A1 | 10/2003 | Roberts |
| 2004/0148278 | A1 | 7/2004 | Milo et al. |
| 2004/0186840 | A1 | 9/2004 | Dettinger et al. |
| 2004/0205050 | A1 | 10/2004 | Stevens et al. |
| 2005/0138160 | A1 | 6/2005 | Klein et al. |
| 2005/0289119 | A1 | 12/2005 | Weinberg et al. |
| 2006/0026189 | A1 | 2/2006 | Djugash et al. |

* cited by examiner

*Primary Examiner* — Apu M Mofiz  
*Assistant Examiner* — Hung D Le  
(74) *Attorney, Agent, or Firm* — Patterson & Sheridan, LLP; Grant A. Johnson

(57) ABSTRACT

Systems and articles of manufacture for managing metadata associated with a data abstraction model abstractly describing data in a database. One embodiment provides a technique for managing metadata describing objects of a data abstraction model with logical fields that define abstract views of physical data in a database. Managing metadata includes traversing a logical tree structure representing the data abstraction model. The logical tree structure has a plurality of nodes, each representing a logical field or a category of logical fields of the data abstraction model. Managing metadata also includes identifying metadata describing logical fields or categories represented by the plurality of nodes. The identified metadata is stored in a queryable database. A user is allowed to query the database to identify objects in the data abstraction model that may be used to construct an abstract query.

10 Claims, 8 Drawing Sheets

METADATA MANAGEMENT FOR A DATA ABSTRACTION MODEL

CROSS-REFERENCE TO RELATED APPLICATIONS

This application is a continuation of U.S. patent application Ser. No. 10/955,467, filed Sep. 30, 2004, by Dettinger et al., which is herein incorporated by reference in its entirety.

BACKGROUND OF THE INVENTION

1. Field of the Invention

The present invention generally relates to managing data abstraction models and, more particularly, to managing metadata associated with a data abstraction model abstractly describing data in a database.

2. Description of the Related Art

Databases are computerized information storage and retrieval systems. The most prevalent type of database is the relational database, a tabular database in which data is defined so that it can be reorganized and accessed in a number of different ways. A distributed database is one that can be dispersed or replicated among different points in a network. An object-oriented programming database is one that is congruent with the data defined in object classes and subclasses.

Regardless of the particular architecture, a database management system (DBMS) can be structured to support a variety of different types of operations for a requesting entity (e.g., an application, the operating system or an end user). Such operations can be configured to retrieve, add, modify and delete information being stored and managed by the DBMS. Standard database access methods support these operations using high-level query languages, such as the Structured Query Language (SQL). The term "query" denominates a set of commands that cause execution of operations for processing data from a stored database. For instance, SQL supports four types of query operations, i.e., SELECT, INSERT, UPDATE and DELETE. A SELECT operation retrieves data from a database, an INSERT operation adds new data to a database, an UPDATE operation modifies data in a database and a DELETE operation removes data from a database.

In commonly assigned U.S. patent application Ser. No. 10/083,075 (the '075 application), filed Feb. 26, 2002 entitled "APPLICATION PORTABILITY AND EXTENSIBILITY THROUGH DATABASE SCHEMA AND QUERY ABSTRACTION", a framework was disclosed for abstractly viewing physical data. The framework of the '075 application provided a requesting entity (i.e., an end-user or application) with a logical representation of physical data. In other words, the framework of the '075 application provided the requesting entity with a data abstraction model that logically describes an underlying physical data structure. In this way, the requesting entity is decoupled from the underlying physical data to be accessed. Thus, changes to the physical data do not necessitate changes to applications accessing the physical data.

Using a data abstraction model according to the framework of the '075 application, abstract queries based on the framework can be constructed without regard for the makeup of the underlying physical data. For instance, assume a user in a hospital who wants to determine last and first names of patients having had a Hemoglobin A1c (HgBA1c) test with a corresponding result value greater than 10%. To this end, the user may specify the following abstract query:

FIND LAST NAME, FIRST NAME
WHERE HGBA1C-RESULT>10

In order to guarantee that the abstract query produces an expected result, the user must ensure that the logical field names "LAST NAME", "FIRST NAME" and "HGBA1C-RESULT" specified in the abstract query correspond to logical field names of respective logical fields in the data abstraction model. However, if the user is not aware of a logical field name of a required logical field, e.g., the "HGBA1C-RESULT" field, the user must retrieve the required logical field from the data abstraction model to determine the corresponding logical field name.

Assume now that there are thousands or even tens or hundreds of thousands of fields in the data abstraction model. Assume further that these thousands or tens or hundreds of thousands of logical fields are grouped into multiple categories. Accordingly, it can be difficult for the user to determine the required logical field. For instance, is a HgbA1c test a hematology test or a body chemistry test? The question is complicated by knowing that there may be 20 different hemoglobin tests based on body locations at which the test is taken, and means of sample extraction. Accordingly, hemoglobin tests can be grouped in a plurality of different categories, each having multiple logical fields. Thus, identifying a required logical field can be a tedious and frustrating process for the user.

Therefore, there is a need for an efficient technique for identifying logical fields from a data abstraction model.

SUMMARY OF THE INVENTION

The present invention is generally directed to techniques for managing data abstraction models and, more particularly, for managing metadata associated with a data abstraction model abstractly describing data in a database.

One embodiment of the invention includes a computer-readable storage medium containing a program which, when executed by a processor, performs operations for generating metadata describing objects of a data abstraction model with logical fields that define abstract views of physical data in a database. The operations may generally include traversing a logical tree structure representing the data abstraction model, the logical tree structure having a plurality of nodes, determining a node type for each node of the plurality of nodes, wherein the node type specifies whether the node is a logical field and a category, and identifying metadata from the data abstraction model describing the plurality of nodes. The operation may further include storing, for each node of the plurality of nodes, the node type and the identified metadata in a queryable database resident on a storage medium and processing a query issued against the queryable database to identify objects in the data abstraction model available to be used to construct an abstract query. The operation of storing the identified metadata in a queryable database may itself generally include creating a first database table configured to allow unique identification of each node contained in the logical tree structure and creating a second database table configured to provide detail information for at least a portion of the nodes identified in the first database table.

Still another embodiment of the invention includes a computer-readable storage medium containing a program which, when executed by a processor, performs operations for generating metadata describing objects of a data abstraction model with logical fields that define abstract views of physical data in a database. The operations may generally include traversing a logical tree structure representing the data abstraction model, the logical tree structure having a plurality of nodes and determining a node type for each node of the plurality of nodes. The node type may specifies whether the node is a logical field and a category. The operations may further include identifying metadata from the data abstraction model describing the plurality of nodes, storing, for each node of the plurality of nodes, the node type and the identified metadata in a queryable database resident on a storage medium, and processing a query issued against the queryable database to identify objects in the data abstraction model available to be used to construct an abstract query. Traversing the logical tree structure itself may include traversing the logical tree structure according to a standard prefix traversal, where the identified metadata comprises standard prefix information for corresponding nodes.

Still another embodiment of the invention includes a computer-readable storage medium containing a program which, when executed by a processor, performs operations for identifying an object in a data abstraction model defining an abstract view of physical data in a database. The operations may generally include providing the data abstraction model. The data abstraction model includes a plurality of objects comprising one or more category specifications and a plurality of logical fields, each logical field defining an abstract view of a specific set of the physical data. The operations may further include receiving a query against one or more database tables containing metadata describing at least some of the plurality of objects, the query configured to identify one or more of the objects by specifying one or more conditions based on the metadata. The operations may also include executing the query, by a processor, to produce a query result identifying one or more of the objects that satisfy the one or more conditions. Executing the query may include accessing a first database table configured to allow unique identification of each logical field and each category specification contained in the data abstraction model. And for each of the one or more objects, determining whether the object is a logical field or a category specification. For each object being a logical field, the operation includes accessing a second database table configured to provide detail information for each logical field of the data abstraction model and retrieving detail information for the object. Further, for each object being a category specification, the operation includes accessing a third database table configured to provide detail information for each category specification of the data abstraction mode and retrieving detail information for the object. The retrieved detail information defines the query result. The operation of the program may also include returning the query result.

Still another embodiment of the invention includes a system having a database and a data abstraction model defining an abstract view of physical data in the database and including a plurality of objects comprising one or more category specifications and a plurality of logical fields, each logical field defining an abstract view of a specific set of the physical data. Additionally, one or more database tables may include metadata describing at least some of the plurality of objects, and the database tables may reside on a storage medium.

The system may also include a data abstraction model metadata manager configured to receive a query against the one or more database tables, the query configured to identify one or more of the objects by specifying one or more conditions based on the metadata. The data abstraction model metadata manager may be further configured to execute the query to produce a query result identifying one or more of the objects that satisfy the one or more conditions. For example, the data abstraction model metadata manager may be configured for accessing a first database table configured to allow unique identification of each logical field and each category specification contained in the data abstraction model and for each of the one or more objects, determining whether the object is a logical field or a category specification. For each object being a logical field, the a data abstraction model metadata manager may access a second database table configured to provide detail information for each logical field of the data abstraction model and retrieve detail information for the object. For each object being a category specification the data abstraction model metadata manager may access a third database table configured to provide detail information for each category specification of the data abstraction model and retrieve detail information for the object. The retrieved detail information may define the query result. Further, the a data abstraction model metadata manager may be configured to return the query result.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Introduction

Figure 1:
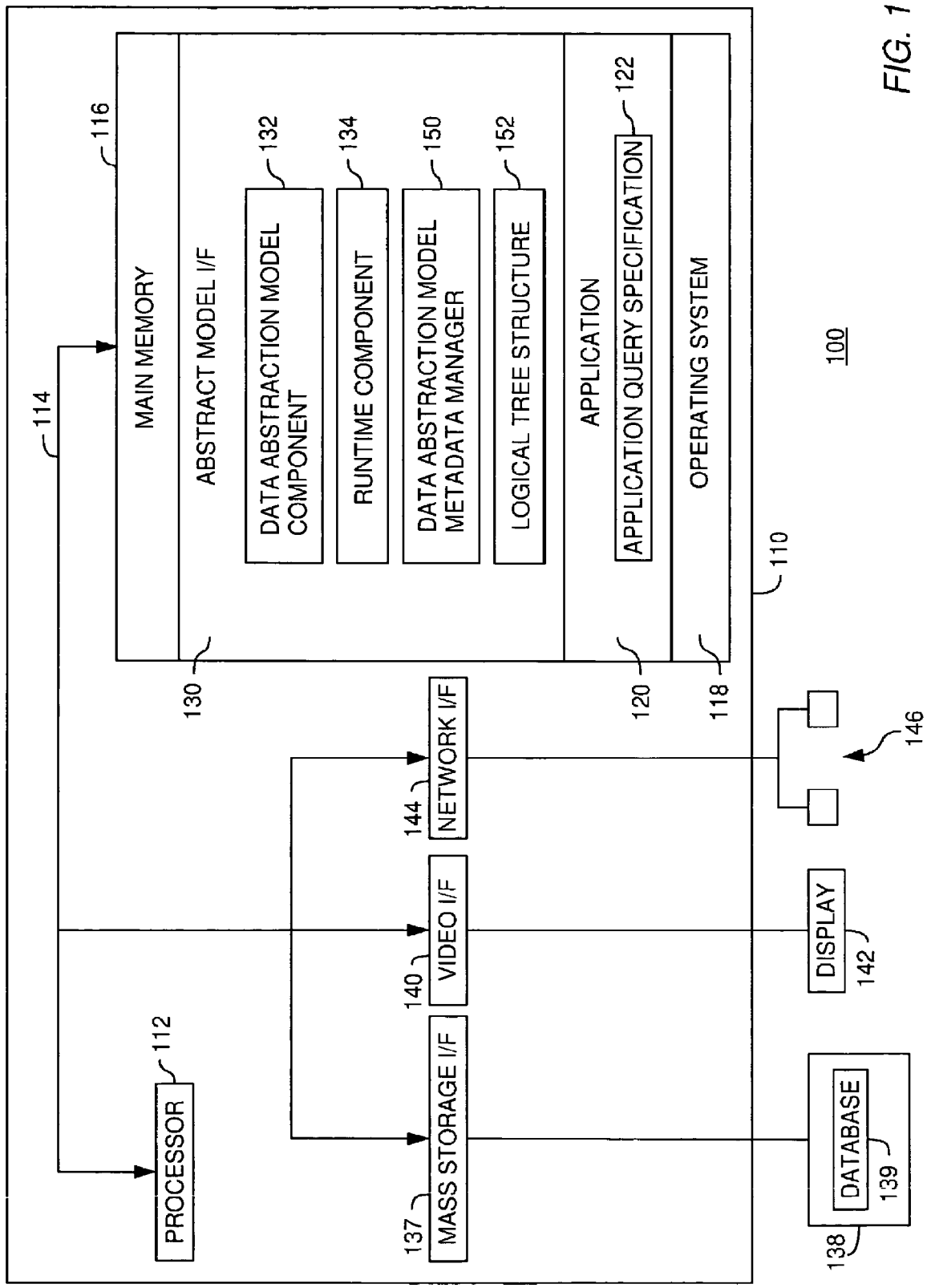
FIG. 1 is a computer system illustratively utilized in accordance with the invention.

The present invention generally is directed to a system, method and article of manufacture for managing data abstraction models and, more particularly, for managing metadata associated with data abstraction models. A data abstraction model defines an abstract view of physical data in a database and includes a plurality of objects, such as logical fields and category specifications. Each logical field defines an abstract view of a specific set of the physical data. Each category specification is provided for a logical grouping of logical fields into a given category. Using the data abstraction model, abstract queries against the physical data in the database can be formulated.

In one embodiment, a data abstraction model is represented by a logical tree structure which is automatically created when loading the data abstraction model to a given computing system. The logical tree structure represents a hierarchical in-memory model of the logical fields and categories of the data abstraction model which are described by corresponding metadata. Accordingly, the logical tree structure includes a plurality of nodes, each representing an object of the data abstraction model, i.e., a logical field or a category of logical fields. Each node is associated with the corresponding metadata which describes the underlying object.

In one embodiment, the metadata is identified by a data abstraction model metadata manager and stored in a queryable database. A user is allowed to query the queryable database to identify objects in the data abstraction model that may be used to construct abstract queries. Accordingly, an efficient technique for identifying objects from a data abstraction model is provided.

Preferred Embodiments

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and, unless explicitly present, are not considered elements or limitations of the appended claims.

One embodiment of the invention is implemented as a program product for use with a computer system such as, for example, computer system 110 shown in FIG. 1 and described below. The program(s) of the program product defines functions of the embodiments (including the methods described herein) and can be contained on a variety of signal-bearing media. Illustrative signal-bearing media include, but are not limited to: (i) information permanently stored on non-writable storage media (e.g., read-only memory devices within a computer such as CD-ROM disks readable by a CD-ROM drive); (ii) alterable information stored on writable storage media (e.g., floppy disks within a diskette drive or hard-disk drive); or (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The software of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular nomenclature that follows is used merely for convenience, and thus the invention should not be limited to use solely in any specific application identified and/or implied by such nomenclature.

An Exemplary Computing Environment

Referring now to FIG. 1, an exemplary computing environment 100 is shown. In general, the distributed environment 100 includes computer system 110 and a plurality of networked devices 146. The computer system 110 may represent any type of computer, computer system or other programmable electronic device, including a client computer, a server computer, a portable computer, an embedded controller, a PC-based server, a minicomputer, a midrange computer, a mainframe computer, and other computers adapted to support the methods, apparatus, and article of manufacture of the invention. In one embodiment, the computer system 110 is an eServer computer available from International Business Machines of Armonk, N.Y.

Illustratively, the computer system 110 comprises a networked system. However, the computer system 110 may also comprise a standalone device. In any case, it is understood that FIG. 1 is merely one configuration for a computer system. Embodiments of the invention can apply to any comparable configuration, regardless of whether the computer system 110 is a complicated multi-user apparatus, a single-user workstation, or a network appliance that does not have non-volatile storage of its own.

The embodiments of the present invention may also be practiced in distributed computing environments in which tasks are performed by remote processing devices that are linked through a communications network. In a distributed computing environment, program modules may be located in both local and remote memory storage devices. In this regard, the computer system 110 and/or one or more of the networked devices 146 may be thin clients which perform little or no processing.

The computer system 110 could include a number of operators and peripheral systems as shown, for example, by a mass storage interface 137 operably connected to a direct access storage device 138, by a video interface 140 operably connected to a display 142, and by a network interface 144 operably connected to the plurality of networked devices 146. The display 142 may be any video output device for outputting viewable information.

Computer system 110 is shown comprising at least one processor 112, which obtains instructions and data via a bus 114 from a main memory 116. The processor 112 could be any processor adapted to support the methods of the invention. The main memory 116 is any memory sufficiently large to hold the necessary programs and data structures. Main memory 116 could be one or a combination of memory devices, including Random Access Memory, nonvolatile or backup memory, (e.g., programmable or Flash memories, read-only memories, etc.). In addition, memory 116 may be considered to include memory physically located elsewhere in the computer system 110, for example, any storage capacity used as virtual memory or stored on a mass storage device (e.g., direct access storage device 138) or on another computer coupled to the computer system 110 via bus 114.

The memory 116 is shown configured with an operating system 118. The operating system 118 is the software used for managing the operation of the computer system 110. Examples of the operating system 118 include IBM OS/400®, UNIX, Microsoft Windows®, and the like.

The memory 116 further includes one or more applications 120 and an abstract model interface 130. The applications 120 and the abstract model interface 130 are software products comprising a plurality of instructions that are resident at various times in various memory and storage devices in the computer system 110. When read and executed by one or more processors 112 in the computer system 110, the applications 120 and the abstract model interface 130 cause the computer system 110 to perform the steps necessary to execute steps or elements embodying the various aspects of the invention.

The applications 120 (and more generally, any requesting entity, including the operating system 118) are configured to issue queries against a database 139 (shown in storage 138). The database 139 is representative of any collection of data regardless of the particular physical representation of the data. A physical representation of data defines an organizational schema of the data. By way of illustration, the database 139 may be organized according to a relational schema (accessible by SQL queries) or according to an XML schema (accessible by XML queries). However, the invention is not limited to a particular schema and contemplates extension to schemas presently unknown. As used herein, the term "schema" generically refers to a particular arrangement of data.

The queries issued by the applications 120 are defined according to an application query specification 122 included with each application 120. The queries issued by the applications 120 may be predefined (i.e., hard coded as part of the applications 120) or may be generated in response to input (e.g., user input). In either case, the queries (referred to herein as "abstract queries") can be composed using logical fields defined by the abstract model interface 130. A logical field defines an abstract view of data whether as an individual data item or a data structure in the form of, for example, a database table or a database column. In particular, the logical fields used in the abstract queries are defined by a data abstraction model 132 of the abstract model interface 130.

Illustratively, the abstract model interface 130 further includes a runtime component 134. Using the data abstraction model 132, the runtime component 134 transforms the abstract queries into concrete queries having a form consistent with the physical representation of the data contained in the database 139. The concrete queries can be executed by the runtime component 134 against the database 139. Operation of the runtime component 134 is further described below with reference to FIG. 2. An exemplary data abstraction model is described below with reference to FIG. 3.

The data abstraction model 132 is also referred to herein as a "logical representation" because the data abstraction model 132 defines logical fields corresponding to data structures in the database 139, thereby providing an abstract, i.e., a logical view of the data in the database 139. A data structure is a physical arrangement of the data, such as an arrangement in the form of a database table or a column of the database table. More specifically, each logical field defines a logical representation of a specific set of the data in the database 139. In a relational database environment having a multiplicity of database tables, a specific logical representation having specific logical fields can be provided for each database table. In this case, all specific logical representations together constitute the data abstraction model 132. Physical entities of the data are arranged in the database 139 according to a physical representation of the data. A physical entity of data (interchangeably referred to as a physical data entity) is a data item in an underlying physical representation. Accordingly, a physical data entity is the data included in a database table or in a column of the database table, i.e., the data itself.

In one embodiment, the data abstraction model 132 is represented by a logical tree structure 152. The logical tree structure 152 is associated with metadata of the data abstraction model 132 which describes logical fields and/or categories of the data abstraction model 132. This metadata can be identified and managed by a data abstraction model metadata manager 150 (hereinafter referred to as "DAM metadata manager", for brevity). Operation of the DAM metadata manager 150 is described below with reference to FIGS. 4-8B.

An Exemplary Query Execution Runtime Environment

Figure 2:
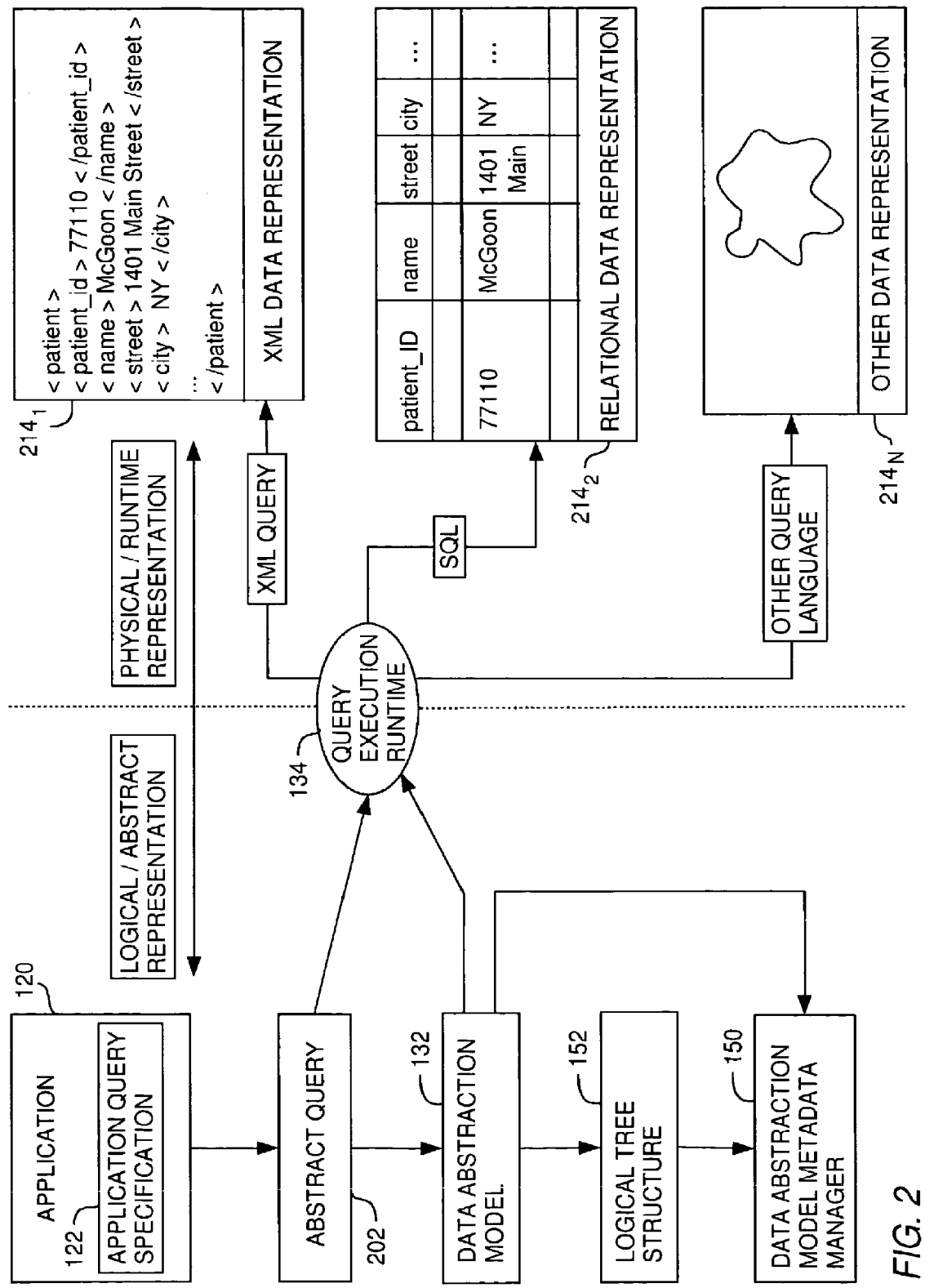
FIGS. 2-3 are relational views of software components according to aspects of the invention.
Figure 3:
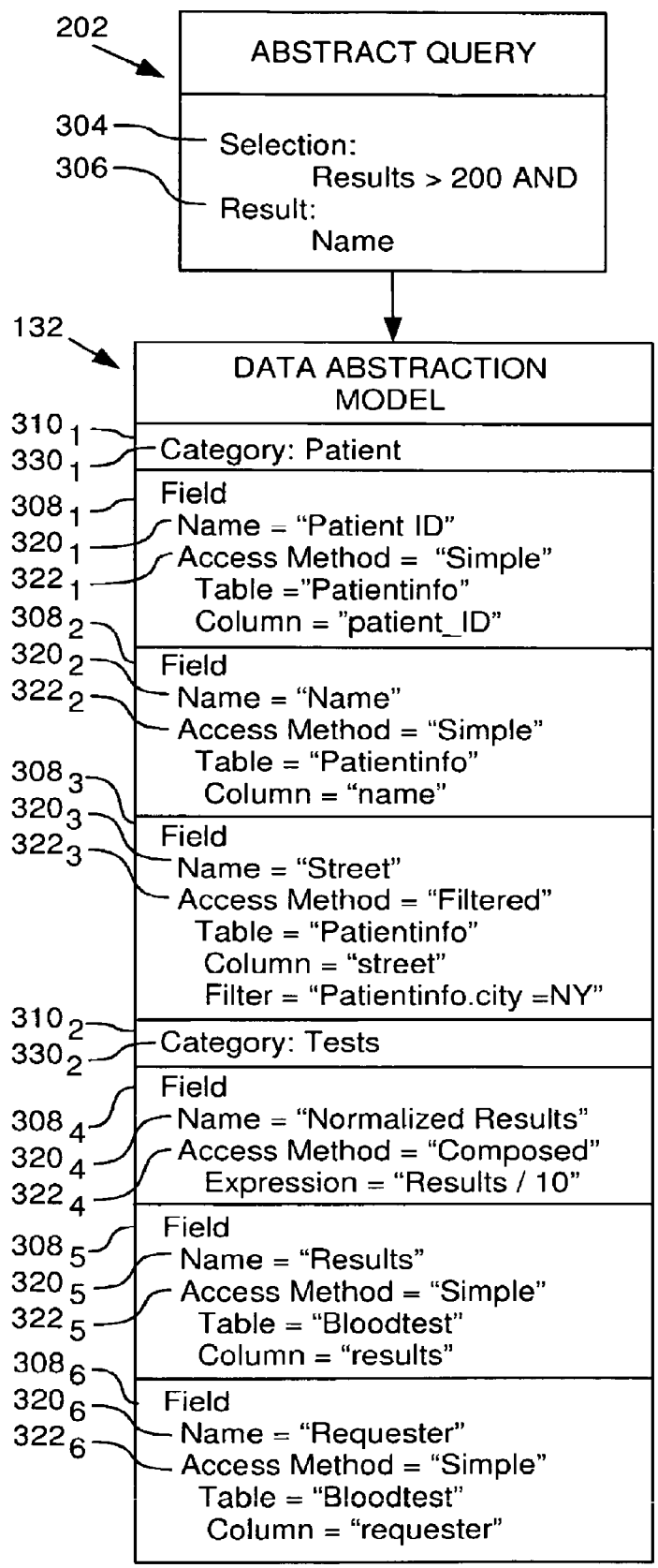

Referring now to FIG. 2, a relational view illustrating interaction of the runtime component 134, the application 120, the data abstraction model 132 and the DAM metadata manager 150 at query execution runtime is shown. Illustratively, the application query specification 122 specifies one or more logical fields using a logical representation of data in a database (e.g., database 139 of FIG. 1) to compose a resulting query 202 against the data. A requesting entity (e.g., the application 120) issues the resulting query 202 as defined by an application query specification of the requesting entity. In one embodiment, the resulting query 202 may include both criteria used for data selection and an explicit specification of result fields to be returned based on the data selection criteria. An example of the selection criteria and the result field specification of the resulting query 202 is shown in FIG. 3. Accordingly, the resulting query 202 illustratively includes selection criteria 304 and a result field specification 306.

The resulting query 202 is generally referred to herein as an "abstract query" because the query is composed according to abstract (i.e., logical) fields rather than by direct reference to the underlying data structures in the database 139. As a result, abstract queries may be defined that are independent of a particular underlying physical data representation used and, thus, loosely coupled to the underlying physical data representation. By way of illustration, two physical data representations are shown, an XML data representation $214_1$ and a relational data representation $214_2$. However, the physical data representation $214_N$ indicates that any other physical data representation, known or unknown, is contemplated.

For execution, the abstract queries are transformed into concrete queries. More specifically, the runtime component 134 is generally configured to transform the abstract query 202 into a concrete query compatible with an underlying physical data representation 214, i.e., the XML representation $214_1$, the SQL representation $214_2$, or any other type of representation $214_N$. To this end, the runtime component 134 maps the logical fields of the abstract query 202 to the corresponding physical fields of the physical data representation 214 using the data abstraction model 132. In one embodiment, a different single data abstraction model 132 is provided for each separate physical representation 214, as explained above for the case of a relational database environment. In an alternative embodiment, a single data abstraction model 132 contains field specifications (with associated access methods) for two or more physical representations 214. A field specification is a description of a logical field and generally comprises a mapping rule that maps the logical field to a data structure(s) of a particular physical representation. The mapping of abstract queries to concrete queries using the data abstraction model 132, by the runtime component 134, is described in detail in the commonly owned, co-pending U.S. patent application Ser. No. 10/083,075, entitled "Application Portability And Extensibility Through Database Schema And Query Abstraction," filed Feb. 26, 2002.

As was noted above, the data abstraction model 132 generally exposes information as a set of logical fields which can be logically grouped into categories of logical fields. According to one aspect, the data abstraction model 132 can be represented by the logical tree structure 152 having a plurality of nodes. Each node represents an object of the data abstraction model, i.e., a logical field or a category of logical fields. An exemplary logical tree structure is described below with reference to FIG. 5. Furthermore, each node is associated with corresponding metadata from the data abstraction model 132 which describes the underlying object. Specifically, the metadata is defined by attributes and properties of attributes of the objects, as described in more detail below with reference to FIG. 3. The metadata can be identified and managed by the DAM metadata manager 150. Operation of the DAM metadata manager 150 is described below with reference to FIGS. 4-8B.

An Exemplary Data Abstraction Model

Referring now to FIG. 3, a relational view illustrating interaction of the abstract query 202 and the data abstraction model 132 is shown. In one embodiment, the data abstraction model 132 comprises a plurality of field specifications $308_1$, $308_2$, $308_3$, $308_4$, $308_5$ and $308_6$ (six shown by way of example), collectively referred to as the field specifications 308. Specifically, a field specification is provided for each logical field available for composition of an abstract query. Each field specification may contain one or more attributes. Illustratively, the field specifications 308 include a logical field name attribute $320_1$, $320_2$, $320_3$, $320_4$, $320_5$, $320_6$ (collectively, field name 320) and an associated access method attribute $322_1$, $322_2$, $322_3$, $322_4$, $322_5$, $322_6$ (collectively, access methods 322). Each attribute may have a value. For example, logical field name attribute $320_1$ has the value "Patient ID" and access method attribute $322_1$ has the value "Simple". In one embodiment, the values of the attributes such as "Patient ID" and "Simple" constitute metadata. Furthermore, each attribute may include one or more associated abstract properties. Each abstract property describes a characteristic of a data structure and has an associated value. The values of the abstract properties also constitute metadata in one embodiment.

As indicated above, a data structure refers to a part of the underlying physical representation that is defined by one or more physical entities of the data corresponding to the logical field. In particular, an abstract property may represent data location information abstractly describing a location of a physical data entity corresponding to the data structure, like a name of a database table or a name of a column in a database table. Illustratively, the access method attribute $322_1$ includes data location information "Table" and "Column". Furthermore, data location information "Table" has the value "Patientinfo" and data location information "Column" has the value "patient_ID". Accordingly, assuming an underlying relational database schema in the present example, the values of data location information "Table" and "Column" point to a table "Patientinfo" having a column "patient_ID". In one embodiment, the values of the data location information, such as "Patientinfo" and "patient_ID" also constitute metadata.

In one embodiment, groups (i.e. two or more) of logical fields may be part of categories. Accordingly, the data abstraction model 132 includes a plurality of category specifications $310_1$ and $310_2$ (two shown by way of example), collectively referred to as the category specifications. In one embodiment, a category specification is provided for each logical grouping of two or more logical fields. For example, logical fields $308_{1-3}$ and $308_{4-6}$ are part of the category specifications $310_1$ and $310_2$, respectively (collectively referred to as "category specifications 310").

A category specification is also referred to herein simply as a "category". The categories are distinguished according to a category name attribute, e.g., category names $330_1$ and $330_2$ (collectively, category name(s) 330) having a corresponding value. In the present illustration, the logical fields $308_{1-3}$ are part of the "Patient" category and logical fields $308_{4-6}$ are part of the "Tests" category. In one embodiment, the values of the attributes of the category specification 310, such as "Patient" and "Tests" also constitute metadata. Each category specification 310 may have additional attributes, such as a group model attribute. In one embodiment, a group model attribute of a given category has a value which indicates how logical fields of the given category are grouped. By way of example, assume an "Individual Name" category related to names of individuals. Assume further that the "Individual Name" category includes a logical field "First Name" directed towards first names of individuals and a logical field "Last Name" directed towards last names of individuals. Assume now that the "Individual Name" category has a group model attribute having a value "AND". In this case, the logical fields "First Name" and "Last Name" for a given individual are logically combined using the Boolean "AND" operator to build the name of the given individual.

The access methods 322 generally associate (i.e., map) the logical field names to data in the database (e.g., database 139 of FIG. 1). Any number of access methods is contemplated depending upon the number of different types of logical fields to be supported. In one embodiment, access methods for simple fields, filtered fields and composed fields are provided. The field specifications $308_1$, $308_2$, $308_5$ and $308_6$ exemplify simple field access methods $322_1$, $322_2$, $322_5$ and $322_6$, respectively. Simple fields are mapped directly to a particular data structure in the underlying physical representation (e.g., a field mapped to a given database table and column). By way of illustration, as described above, the simple field access method $322_1$ maps the logical field name $320_1$ ("Patient ID") to a column named "patient_ID" in a table named "Patientinfo". The field specification $308_3$ exemplifies a filtered field access method $322_3$. Filtered fields identify an associated data structure and provide filters used to define a particular subset of items within the physical representation. An example is provided in FIG. 3 in which the filtered field access method $322_3$ maps the logical field name $320_3$ ("Street") to data in a column named "street" in the "Patientinfo" table and defines a filter for individuals in the city of "NY". Another example of a filtered field is a New York ZIP code field that maps to the physical representation of ZIP codes and restricts the data only to those ZIP codes defined for the state of New York. The field specification $308_4$ exemplifies a composed field access method $322_4$. Composed access methods compute a logical field from one or more data structures using an expression supplied as part of the access method definition. In this way, information which does not exist in the underlying physical data representation may be computed. In the example illustrated in FIG. 3 the composed field access method $322_4$ maps the logical field name $320_4$ "Normalized Results" to "Results/10". Another example is a sales tax field that is composed by multiplying a sales price field by a sales tax rate. In one embodiment, the values of the access methods 322, such as "Simple", "Filtered" and "Composed" also constitute metadata.

It should be noted that in the context of the present invention the term "metadata" is used to designate any data that describes a logical field or a category specification of a given data abstraction model or characteristics thereof. Accordingly, in the given example the metadata includes all data contained in the data abstraction model 132. Specifically, the metadata includes all values of any attributes and abstract properties provided in the logical field specifications 308 and the category specifications 310, such as category names, logical field names, access methods and data location information.

It is contemplated that the formats for any given data type (e.g., dates, decimal numbers, etc.) of the underlying data may vary. Accordingly, in one embodiment, the field specifications 308 include a type attribute which reflects the format of the underlying data. However, in another embodiment the data format of the field specifications 308 is different from the associated underlying physical data, in which case a conversion of the underlying physical data into the format of the logical field is required.

By way of example, the field specifications 308 of the data abstraction model 132 shown in FIG. 3 are representative of logical fields mapped to data represented in the relational data representation 214₂ shown in FIG. 2. However, other instances of the data abstraction model 132 map logical fields to other physical representations, such as XML.

As was noted above, the logical fields of the data abstraction model 132 can be used to build the abstract query 202. An illustrative abstract query corresponding to the abstract query 202 shown in FIG. 3 is shown in Table I below. By way of illustration, the illustrative abstract query is defined using XML. However, any other language may be used to advantage.

TABLE I

ABSTRACT QUERY EXAMPLE

```
001  <?xml version="1.0"?>
002  <!--Query string representation: (Results > "200"-->
003  <QueryAbstraction>
004    <Selection>
005      <Condition internalID="4">
006      <Condition field="Results" operator="GT" value="200"
007          internalID="1"/>
008    </Selection>
009    <Results>
010      <Field name="Name"/>
011    </Results>
012  </QueryAbstraction>
```

Illustratively, the abstract query shown in Table I includes a selection specification (lines 004-008) containing selection criteria and a result specification (lines 009-011). In one embodiment, a selection criterion (hereinafter also referred to as "search criterion") consists of a field name (for a logical field), a comparison operator (=, >, <, etc) and a value expression (what is the field being compared to). In one embodiment, the result specification is a list of abstract fields that are to be returned as a result of query execution. A result specification in the abstract query may consist of a field name and sort criteria.

An illustrative data abstraction model (DAM) corresponding to the data abstraction model 132 shown in FIG. 3 is shown in Table II below. By way of illustration, the illustrative data abstraction model is defined using XML. However, any other language may be used to advantage.

TABLE II

DATA ABSTRACTION MODEL EXAMPLE

```
001  <?xml version="1.0"?>
002  <DataAbstraction>
003    <Category name="Patient">
004      <Field queryable="Yes" name="Patient ID" displayable="Yes">
005        <AccessMethod>
006          <Simple columnName="patient_ID" tableName="Patientinfo"></Simple>
007        </AccessMethod>
008      </Field>
009      <Field queryable="Yes" name="Name" displayable="Yes">
010        <AccessMethod>
011          <Simple columnName="name" tableName="Patientinfo"></Simple>
012        </AccessMethod>
013      </Field>
014      <Field queryable="Yes" name="Street" displayable="Yes">
015        <AccessMethod>
016          <Filter columnName="street" tableName="Patientinfo">
017          </Filter="Patientinfo.city=NY">
018        </AccessMethod>
019      </Field>
020    </Category>
021    <Category name="Tests">
022      <Field queryable="Yes" name="Normalized Results" displayable="Yes">
023        <AccessMethod>
024          <Composed columnName="results" tableName="Bloodtest">
025          </Composed Expression="Results/10">
026        </AccessMethod>
027      </Field>
028      <Field queryable="Yes" name="Results" displayable="Yes">
029        <AccessMethod>
030          <Simple column Name="results" tableName="Bloodtest"></Simple>
031        </AccessMethod>
032      </Field>
033      <Field queryable="Yes" name="Requester" displayable="Yes">
034        <AccessMethod>
035          <Simple columnName="requester" tableName="Bloodtest"></Simple>
036        </AccessMethod>
037      </Field>
038    </Category>
039  </DataAbstraction>
```

By way of example, note that lines 004-008 correspond to the first field specification 308₁ of the DAM 132 shown in FIG. 3 and lines 009-013 correspond to the second field specification 308₂.

As was noted above, a data abstraction model can be represented by a logical tree structure which is associated with corresponding metadata from the data abstraction model. The metadata can be identified and managed by a DAM metadata manager. Operation of an exemplary DAM metadata manager is described below with reference to FIG. 4.

An Exemplary Operation of a DAM Metadata Manager

Figure 4:
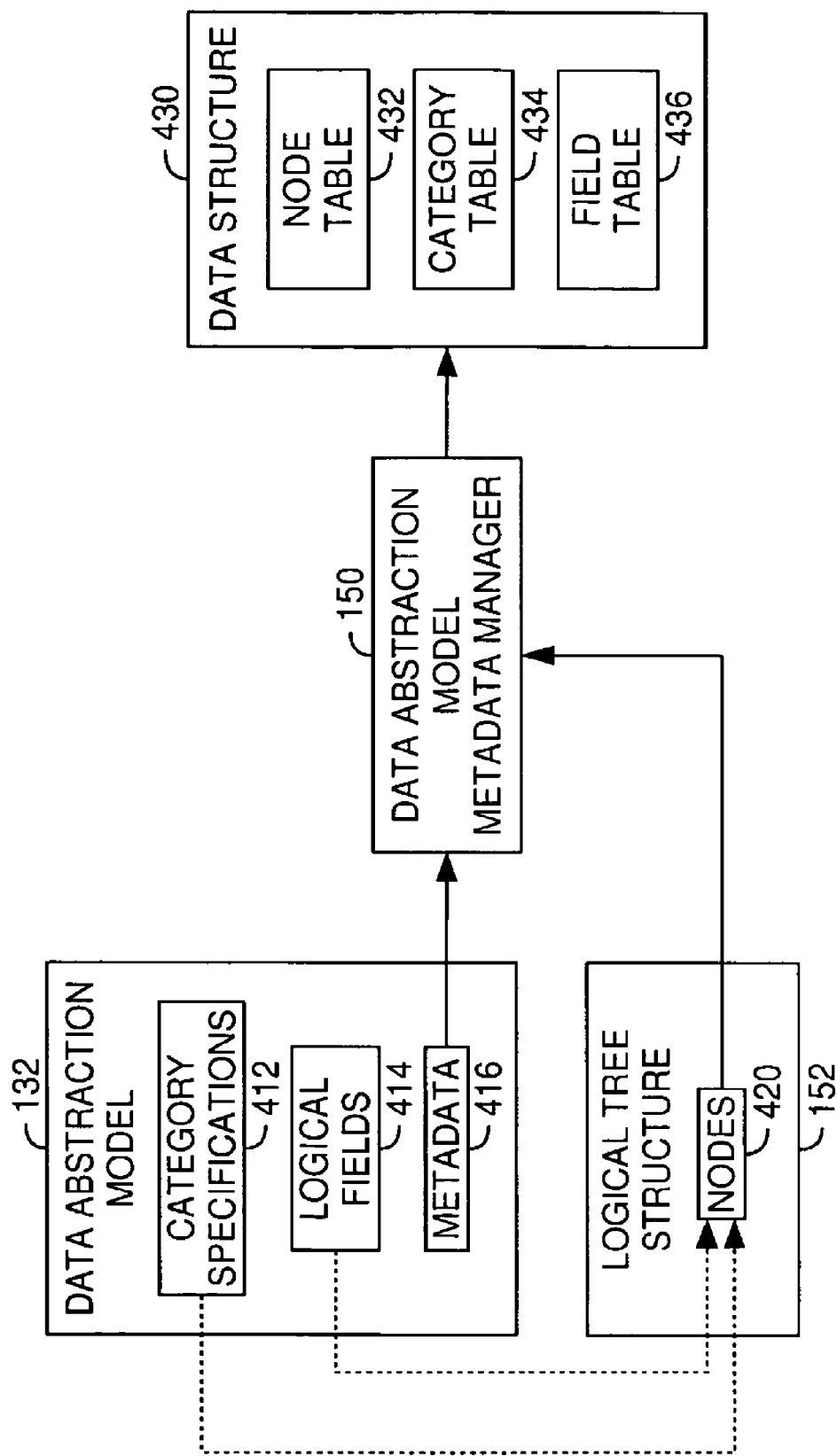
FIG. 4 is a relational view illustrating operation of a data abstraction model metadata manager in one embodiment.

Referring now to FIG. 4, a relational view of components implementing one aspect of the invention is illustrated. The components illustratively include the data abstraction model 132, the logical tree structure 152 and the DAM metadata manager 150 of FIG. 1. The components further include an illustrative data structure 430.

As was noted above, the data abstraction model 132 includes a plurality of logical fields 414. The data abstraction model 132 may further include one or more category specifications 412 defining one or more categories of logical fields. The logical fields 414 and the category specifications 412 are described by metadata 416. The data abstraction model 132 is represented by the logical tree structure 152 which includes a plurality of nodes 420. Each of the nodes 420 represents one of the logical fields 414 or one of the categories 412. An exemplary logical tree structure is described below with reference to FIG. 5.

The DAM metadata manager 150 is configured to manage the data structure 430. More specifically, the DAM metadata manager 150 is configured to identify at least a portion of the nodes 420 from the logical tree structure 152 and metadata from the metadata 416 of the data abstraction model 132 that is associated with the identified nodes. The DAM metadata manager 150 is further configured to store information about the identified nodes and the identified metadata in the data structure 430. Illustratively, the data structure 430 includes a node table 432 for storing the information about the identified nodes, a category table 434, and a field table 436 for storing the identified metadata. The data structure 430 is queryable in order to allow a user to identify objects in the data abstraction model 132 that may be used to construct an abstract query.

In one embodiment, the DAM metadata manager 150 creates the node table 432 before identification of the nodes from the plurality of nodes 420 and, subsequently, the category table 434 and the field table 436 before identification of the associated metadata. For instance, after creation of the node table 432, the DAM metadata manager 150 identifies each of the nodes 420 from the logical tree structure 152 and stores corresponding descriptive information in the node table 432. The descriptive information allows for a unique identification of each of the nodes 420 contained in the logical tree structure 152. Subsequently, the DAM metadata manager 150 creates the category table 434 and the field table 436. Then, the DAM metadata manager 150 uses the node table 432 and the data abstraction model 132 to identify the associated metadata with respect to the identified nodes. The associated metadata is stored in the category table 434 and the field table 436. More specifically, the DAM metadata manager 150 stores detail information for each node identified in the node table 432 which represents one of the category specifications 412 of the data abstraction model 132 in the category table 434. In the field table 436, the DAM metadata manager 150 stores detail information for each node identified in the node table 432 which represents one of the logical fields 414 of the data abstraction model 132.

However, it should be noted that subsequent creation of the node, category and field tables by the DAM metadata manager 150 has merely been described by way of example and not for limiting the invention accordingly. Instead, the DAM metadata manager 150 may create the node, category and field tables in an arbitrary order of sequence or even simultaneously. Alternatively, the DAM metadata manager 150 may use predefined node, category and field tables. More specifically, as was noted above, the descriptive information which is stored in the node table 432 is determined from the logical tree structure 152 and the detail information which is stored in the category table 434 and the field table 436 is determined from the data abstraction model 132. Accordingly, the logical tree structure 152 and the data abstraction model 132 can be analyzed to determine which columns need to be included with the node table 432, the category table 434 and the field table 436 to accommodate the descriptive/detail information. In this case, the node table 432, the category table 434 and the field table 436 can be provided as template tables which are subsequently filled with the descriptive/detail information, as described in more detail below with reference to FIGS. 6A-C.

An Exemplary Logical Tree Structure

Figure 5:
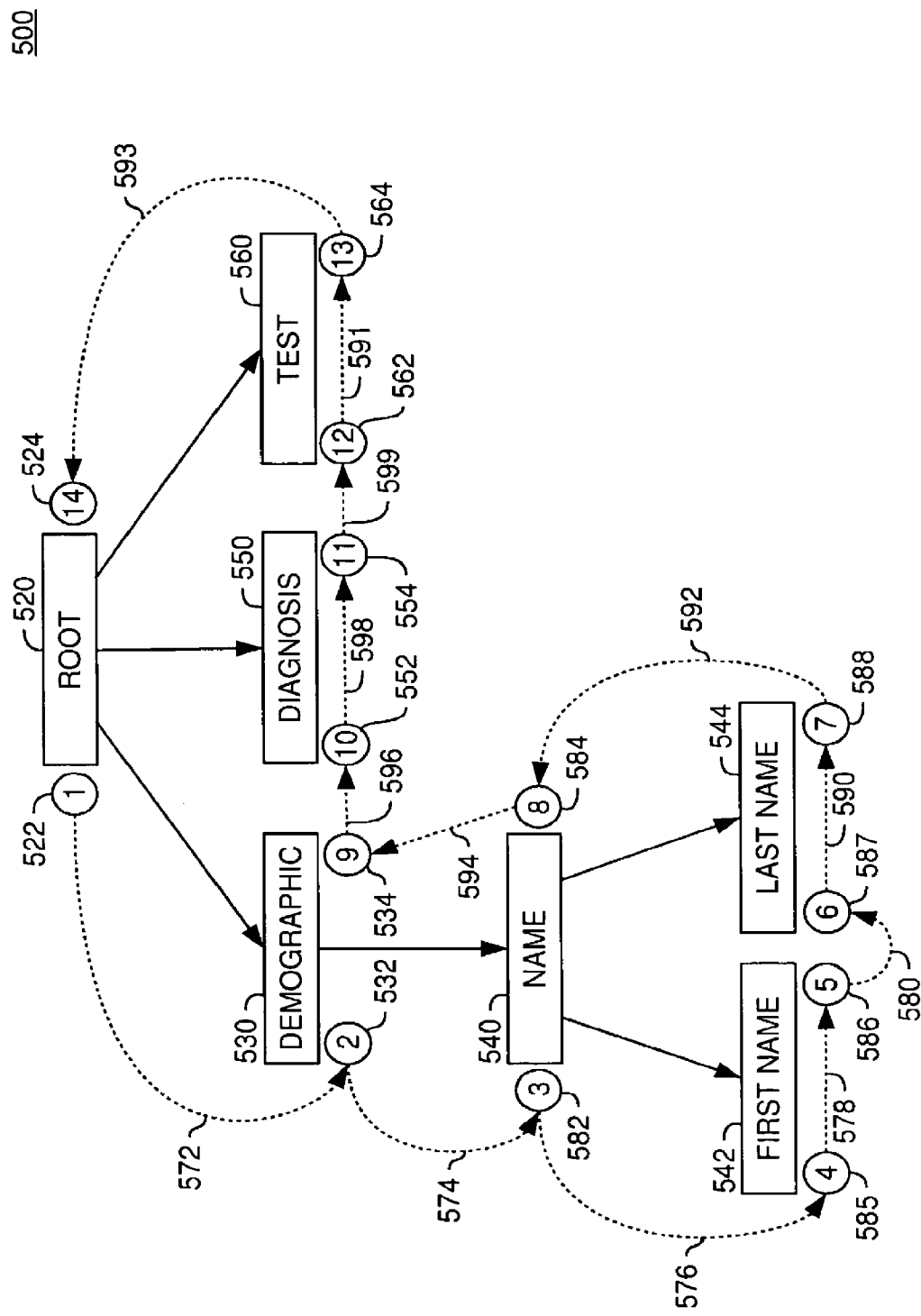
FIG. 5 is a logical tree structure representing a data abstraction model in one embodiment.
Figure 6:
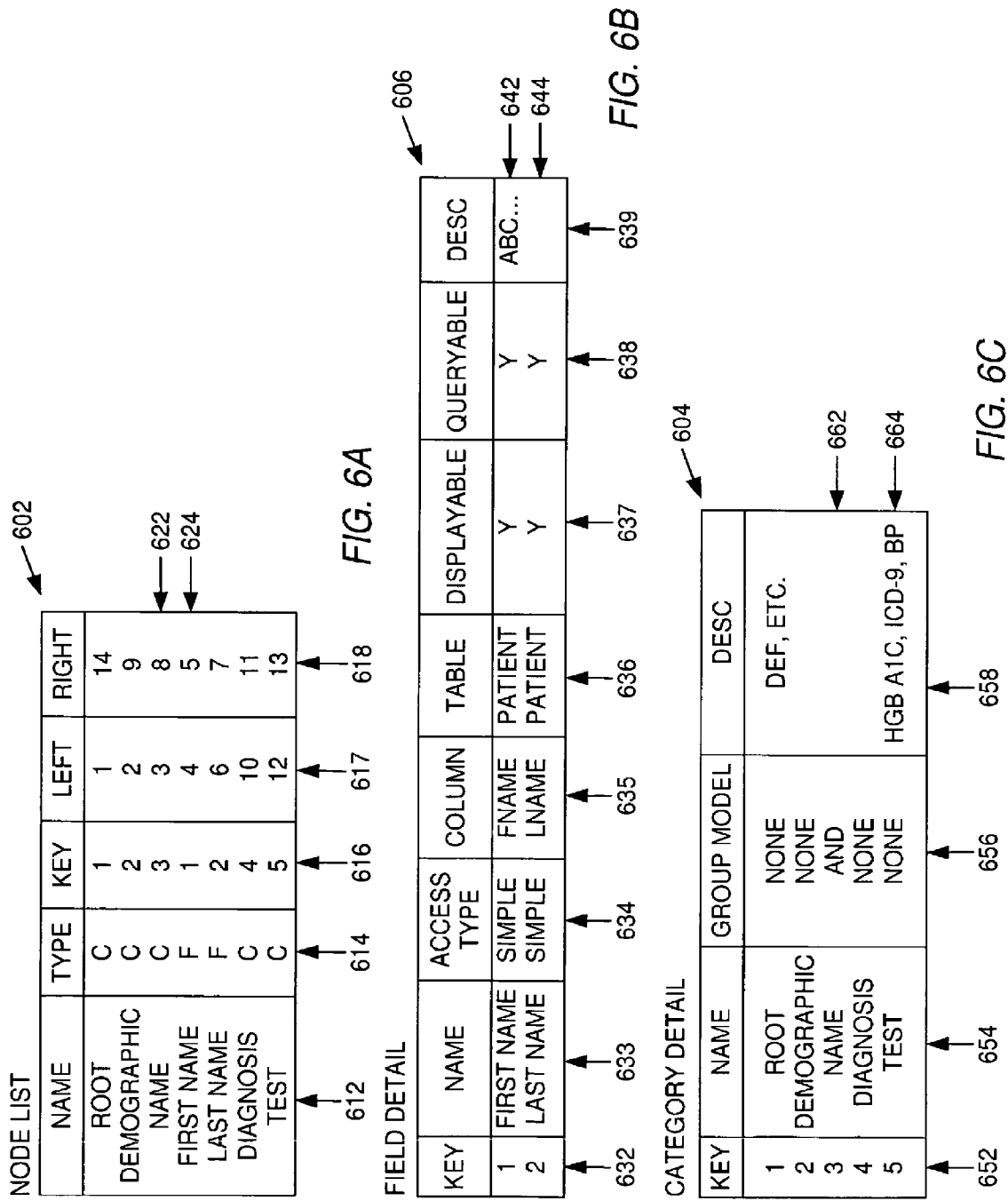
FIGS. 6A-C are database tables illustrating metadata identified from the exemplary logical tree structure of FIG. 5 in one embodiment.

Referring now to FIG. 5, an exemplary logical tree structure 500 (e.g., logical tree structure 152 of FIG. 4) representing an underlying data abstraction model (e.g., data abstraction model 132 of FIG. 4) is illustrated. For purposes of illustration, it is assumed that the underlying data abstraction model includes a plurality of category specifications (e.g., category specifications 412 of FIG. 4 or 310 of FIG. 3) and a plurality of logical fields (e.g., logical fields 414 of FIG. 4 or 308 of FIG. 3). More specifically, assume that the underlying data abstraction model includes a "Demographic", a "Diagnosis" and a "Test" category. The "Demographic" category relates to information about patients in a hospital, the "Diagnosis" category relates to information about diagnoses which have been established for the patients, and the "Test" category relates to information about tests which have been performed on the patients in order to establish the diagnoses. Assume further that the "Demographic" category includes a "Name" category which includes a logical field "First Name" and a logical field "Last Name". For instance, the "Name" category relates to names of the patients and the "First Name" and "Last Name" logical fields refer to first and last names. Assume also that the "Last Name" logical field refers to a "lname" column in a database table "Patient" that contains last names of the patients and the "First Name" logical field refers to a "fname" column in the "Patient" table that contains corresponding first names. For brevity, the "Diagnosis" and "Test" categories of the underlying data abstraction model are not described in more detail.

Illustratively, the exemplary logical tree structure 500 includes a single root node 520 and a plurality of other nodes 530, 540, 542, 544, 550 and 560. The root node 520 represents the highest level in the logical tree structure 500 and defines a starting point for traversal of the logical tree structure 520. However, the root node 520 does not represent any logical field or category, while each of the plurality of nodes 530, 540, 542, 544, 550 and 560 represents a particular logical field or category of the underlying data abstraction model.

In one embodiment, the nodes 530, 540, 542, 544, 550 and 560 define different logical branches, each of which joins the root node 520. Illustratively, a first logical branch represents the "Demographic" category of the underlying data abstraction model and includes nodes 530, 540, 542 and 544. A second logical branch includes node 550 which represents the "Diagnosis" category. A third logical branch includes node 560 which represents the "Test" category. More specifically, the first logical branch includes a top-parent node 530 "Demographic" that represents the "Demographic" category. The top-parent node 530 has associated child nodes 540, 542 and 544. The child nodes 540, 542 and 544 represent objects which are contained in the "Demographic" category of the underlying data abstraction model. The child node 540 "Name" illustratively represents the "Name" category that is included with the "Demographic" category. Moreover, the node 540 is a parent node for the child nodes 542 and 544. Accordingly, the child nodes 542 and 544 represent objects which are contained in the "Name" category of the "Demographic" category of the underlying data abstraction model. More specifically, the child node 542 illustratively represents the logical field "First Name". The child node 542 illustratively represents the logical field "Last Name".

It should be noted that the logical tree structure 500 represents a single underlying data abstraction model, wherein each logical branch corresponds to a category of the underlying data abstraction model. However, in one embodiment a plurality of data abstraction models is provided. In this case, each data abstraction model can be represented by a corresponding logical branch. In other words, various approaches are suitable for representing one or more data abstraction models as a logical tree structure. All such approaches are broadly contemplated.

In one embodiment, the logical tree structure 500 is traversed to identify each node contained therein. Techniques for traversing logical tree structures are well-known in the art and any suitable technique, known or unknown, can be used to traverse the logical tree structure 500. By way of example, assume that the logical tree structure 500 is traversed using a standard prefix traversal. Accordingly, standard prefix information is determined from the logical tree structure 500. The determined standard prefix information is then stored in a corresponding node table (e.g., node table 432 of FIG. 4). An exemplary node table 602 representing the corresponding node table in the given example is illustrated in FIG. 6A.

Referring now to FIG. 6A, the node table 602 includes a data record (i.e., a row) for each of the nodes 520, 530, 540, 542, 544, 550 and 560. Illustratively, the node table 602 includes a plurality of columns 612, 614, 616, 617 and 618. By way of example, the column 612 includes an identifier for each node, such as a category or field name. The column 614 includes a node type indicator for each node, such as "c" for category or "f" for field. The column 616 includes a key for each node, such as a numeric number. According to one aspect, the node type indicator and the key are configured such that a combination of both defines a unique identifier for each data record and, thus, for each of the nodes 520, 530, 540, 542, 544, 550 and 560. The column 617 includes a left indicator and the column 618 includes a right indicator for each node. The left and the right indicators are used to delineate nested set hierarchy notation for the nodes 520, 530, 540, 542, 544, 550 and 560. Determination of the data records contained in the node table 602 is now described with reference back to FIG. 5.

As was noted above, the data records of the node table 602 can be determined by traversing the logical tree structure 500 using a standard prefix traversal. The standard prefix traversal starts at the root node 520. Then, all branches of the logical tree structure 500 are traversed from a top-level parent node of each branch down to a bottom-level node of the branch. In the given example, the root node 520 is arbitrarily classified as a "c" type node, i.e., as a category type node. As the root node 520 is the first node of the traversal, a key "1" is associated with the root node 520. Then, departing from a left indicator 522 of the root node 520, the logical branches of the logical tree structure 500 are traversed. The left indicator 522 of the root node 520 is set to "1". Then, left and right indicators for each traversed node are determined by incrementing a previously traversed left or right indicator by "1".

Illustratively, the traversal departs from the left indicator 522 "1" of the root node 520 and continues to a left indicator 532 of the top-parent node 530 "Demographic" of the first logical branch, as illustrated by a dashed arrow 572. The left indicator 532 is determined by incrementing the previously traversed indicator, i.e., the left indicator 522 "1", by "1". Accordingly, the left indicator 532 is set to "2". The "Demographic" node 530 is the second traversed category (i.e., "c") type node and is, thus, associated with a key "2". Traversal then continues from the left indicator 532 to a left indicator 582 "3" of the node 540 "Name", as illustrated by a dashed arrow 574.

The "Name" node 540 is the third traversed category (i.e., "c") type node and is, thus, associated with a key "3". Traversal then continues from the left indicator 582 to a left indicator 585 "4" of the node 542 "First Name", as illustrated by a dashed arrow 576. The "First Name" node 542 is the first traversed logical field (i.e., "f") type node and is, thus, associated with a key "1". As the node 542 has no child node, a right indicator 586 of the node 542 is set to "5". Traversal then continues from the left indicator 585 to the right indicator 586, as illustrated by a dashed arrow 578. Normally, traversal then continues from the right indicator 586 to the parent node of the "First Name" node 542, i.e., the "Name" node 540. There, it is determined whether the parent node "Name" 540 has another child and, if so, traversal continues at a left indicator of that other child. Illustratively, the "Name" node 540 has a second child, i.e., the "Last Name" node 544 having a left indicator 587 "6". However, for brevity it is illustrated that traversal continues from the right indicator 586 immediately at the left indicator 587 "6" of the node 544 "Last Name", as illustrated by a dashed arrow 580. The "Last Name" node 544 is the second traversed logical field (i.e., "f") type node and is, thus, associated with a key "2". As the node 544 has also no child node, a right indicator 588 of the node 544 is set to "7". The right indicator 588 is traversed from the left indicator 587, as illustrated by a dashed arrow 590.

As the node 540 "Name" has no other child nodes, the traversal continues at a right indicator 584 of the "Name" node 540, as illustrated by a dashed arrow 592. Accordingly, the right indicator 584 is set to "8". As the node 530 "Demographic" has no other child nodes, the traversal continues at a right indicator 534 of the "Demographic" node 530, as illustrated by a dashed arrow 594. The right indicator 534 is, thus, set to "9". Accordingly, when reaching the right indicator 534, the first logical branch has been traversed.

Traversal then returns to the root node 520, from where the second logical branch is entered. However, for brevity a dashed arrow 596 indicates that traversal continues from the right indicator 534 immediately at a left indicator 552 of the "Diagnosis" node 550. The left indicator 552 is set to "10" by incrementing the right indicator 534 "9" of the "Demographic" node by "1". As the "Diagnosis" node 550 is the fourth traversed category (i.e., "c") type node, it is associated with a key "4". As the "Diagnosis" node 530 has no child nodes, the traversal continues at a right indicator 554 of the "Diagnosis" node 550, as illustrated by a dashed arrow 598. The right indicator 554 is, thus, set to "11". Accordingly, when reaching the right indicator 554, the second logical branch has been traversed.

Traversal then returns to the root node 520, from where the third logical branch is entered. However, for brevity a dashed arrow 599 indicates that traversal continues from the right indicator 554 immediately at a left indicator 562 of the "Test" node 560. The left indicator 562 is set to "12". As the "Test" node 560 is the fifth traversed category (i.e., "c") type node, it is associated with a key "5". As the "Test" node 560 has no child nodes, the traversal continues at a right indicator 564 of the "Test" node 560, as illustrated by a dashed arrow 591. The right indicator 564 is set to "13". As the root node 520 has no other child nodes, i.e., there are no other logical branches, the traversal completes at a right indicator 524 of the root node 520, as illustrated by a dashed arrow 593. The right indicator 524 is set to "14".

It should be noted that the left and right indicators are determined such that a node having left and right indicators which define an interval of numbers that includes left and right indicators of one or more other nodes is a parent node of the one or more other nodes. For instance, in the given example the left indicator 582 "3" and the right indicator 584 "8" of the "Name" node define the range [3; 8]. As the left and right indicators of the "First Name" and "Last Name" nodes (i.e., "4", "5", "6", and "7", respectively) fall into this interval, this indicates that the "Name" node is the parent node of the "First Name" and "Last Name" nodes, as mentioned above.

As was noted above, the standard prefix information which is determined by traversing the logical tree structure 500 as described above is stored in the node table 602 of FIG. 6A. Illustratively, the standard prefix information which has been determined for the "Name" node 540 is stored in a row 622 of the node table 602. The standard prefix information which has been determined for the "First Name" node 542 is stored in a row 624.

Subsequently, metadata (e.g., metadata 416 of FIG. 4) is identified from the underlying data abstraction model for each node described in the node table 602. In one embodiment, the metadata which is identified for a field type node is stored in a field table (e.g., field table 436 of FIG. 4). The metadata which is identified for a category type node is stored in a category table (e.g., category table 434 of FIG. 4). An exemplary field table is described below with reference to FIG. 6B. An exemplary category table is described below with reference to FIG. 6C.

Referring now to FIG. 6B, an exemplary field table 606 is illustrated. The exemplary field table 606 illustratively includes two data records 642 and 644. The data records 642 and 644 contain exemplary detail information for the logical fields "First Name" and "Last Name", which are represented in FIG. 5 by nodes 542 and 544, respectively.

Illustratively, the exemplary field table 606 includes a plurality of columns 632, 633, 634, 635, 636, 637, 638 and 639. By way of example, the column 632 includes a key for each logical field. The keys correspond to the respective keys in the node table 602 of FIG. 6A. The column 633 includes a logical field name for each logical field. The column 634 includes an access type (also referred to herein as "access method") for each logical field. The column 635 includes for each logical field an identifier of a column in a database table, which is accessed by the logical field, such as a column name. The column 636 includes corresponding identifiers of the accessed database tables, such as table names. The column 637 includes a value of a "Displayable" attribute for each logical node and the column 638 includes a value of a "Queryable" attribute. The column 639 includes some descriptive text for each logical field.

In the given example, the data record 642 for the logical field "First Name" associates the key "1" with the logical field name "First Name". Furthermore, the data record 642 indicates that data associated with the "First Name" field can be determined by accessing, using an access type "simple", the column "fname" in the database table "Patient". The data record 642 further indicates that the logical field "First Name" is displayable ("Y" in column 637) and queryable ("Y" in column 638). The data record 642 also includes some descriptive text in column 639 ("ABC") which describes the logical field "First Name". The logical field "Last Name" is described in a similar manner by the data record 644.

However, it should be noted that the columns 632, 633, 634, 635, 636, 637, 638 and 639 have merely been described by way of example and are not intended to limit the invention accordingly. Specifically, the number and content of columns in the field table 606 may vary dependent on the underlying logical field specifications (e.g., logical field specifications 308 of FIG. 3). For instance, the underlying logical field specifications may be provided without a "Queryable" attribute. In this case, the column 638 can be dropped. Moreover, as specific logical fields can be defined according to a "Filtered" access type, a column containing filter definitions can be required. However, in this case data records which are related to logical fields having a "Simple" access type would have no value or a null value in a corresponding filter definition column. Thus, any implementation of the field table 606 which is suitable for storing detail information with respect to logical fields of an underlying, known or unknown, data abstraction model are broadly contemplated.

Referring now to FIG. 6C, an exemplary category table 604 is illustrated. The exemplary category table 604 illustratively includes a plurality of data records, such as data records 662 and 664. Each data record contains exemplary detail information for the categories, which are represented in FIG. 5 by nodes 520, 530, 540, 550 and 560.

Illustratively, the exemplary category table 604 includes a plurality of columns 652, 654, 656 and 658. By way of example, the column 652 includes a key for each category. The keys correspond to the respective keys in the node table 602 of FIG. 6A. The column 654 includes a category name for each category. The column 656 includes a value of a "Group Model" attribute for each category. The column 658 includes some descriptive text for each category.

In the given example, the data record 662 for the category "Name" associates the key "3" with the category name "Name". The group model value "AND" in column 656 of the data record 662 indicates that all logical fields contained in the category "Name" are combined by a Boolean AND operator. In other words, values of the logical fields "First Name" AND "Last Name" constitute full names of patients. The data record 662 also includes some descriptive text in column 658 ("DEF") which describes the category "Name". The category "Test" is described in a similar manner by the data record 664. Specifically, the data record 664 for the category "Test" includes descriptive test which describes, in the given example, a list of different medical tests, i.e., "HgbA1c", "ICD-9" and "BP". Assume that this descriptive text indicates that the "Test" category contains information relating to the specified tests.

However, it should be noted that the columns 652, 654, 656 and 658 have merely been described by way of example and are not intended to limit the invention accordingly. Specifically, the number and content of columns may vary dependent on the underlying category specifications (e.g., category specifications 310 of FIG. 3). For instance, the underlying category specifications may be provided without a "Group Model" attribute. In this case, the column 656 can be dropped. Thus, any implementation of the category table 604 is broadly contemplated.

An Exemplary Method for Managing Dam Metadata

Figure 7:
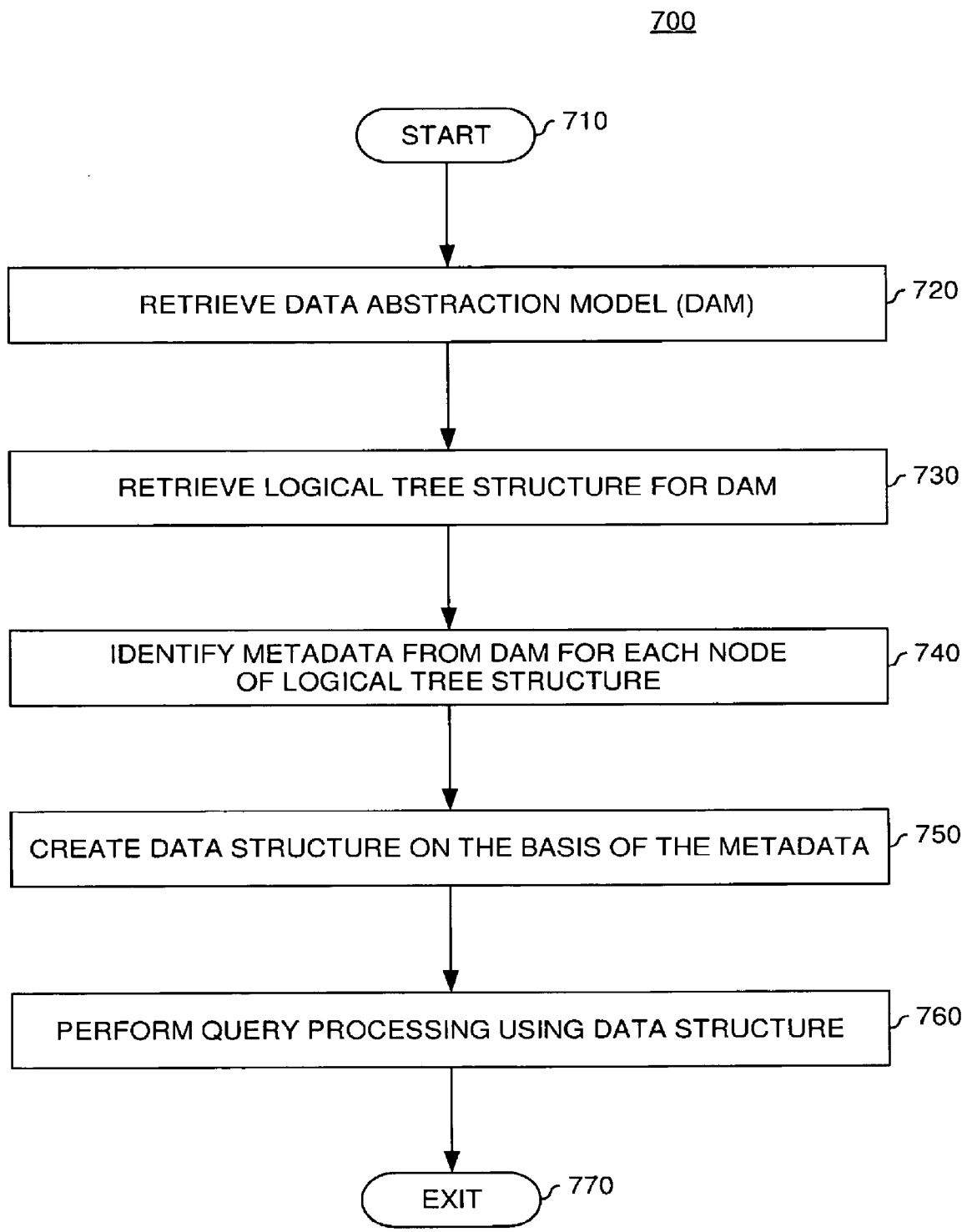
FIG. 7 is a flow chart illustrating a method of managing metadata describing objects of a data abstraction model in one embodiment.

Referring now to FIG. 7, an exemplary method 700 for managing metadata (e.g., metadata 416 of FIG. 4) describing objects of a data abstraction model (e.g., data abstraction model 132 of FIG. 4) is illustrated. In one embodiment, at least part of the steps of method 700 is performed by a DAM metadata manager (e.g., DAM metadata manager 150 of FIG. 4). Method 700 starts at step 710.

At step 720, an underlying data abstraction model (e.g., data abstraction model 132 of FIG. 4) having a plurality of category specifications (e.g., category specifications 412 of FIG. 4) and logical fields (e.g., logical fields 414 of FIG. 4) is retrieved. At step 730, a logical tree structure (e.g., logical tree structure 152 of FIG. 4) having a plurality of nodes (e.g., nodes 420 of FIG. 4) which represent the category specifications and logical fields of the underlying data abstraction model is retrieved.

At step 740, the logical tree structure is traversed and metadata describing the logical fields and categories represented by the plurality of nodes is identified from the underlying data abstraction model. At step 750, a queryable data structure (e.g., data structure 430 of FIG. 4) such as a queryable database (e.g., node table 432, category table 434 and field table 436 of FIG. 4) is created. The identified metadata is stored in the queryable database. Moreover, a user is allowed to query the queryable database to identify objects in the data abstraction model that may be used to construct an abstract query.

In one embodiment, creating the queryable data structure includes creating a particular data abstraction model (hereinafter referred to as "metadata abstraction model") on the basis of the queryable database. Accordingly, abstract queries can be issued against the metadata abstraction model. The creation of abstract queries and data abstraction models is described in detail in the commonly owned, co-pending U.S. patent application Ser. No. 10/083,075, entitled "Application Portability And Extensibility Through Database Schema And Query Abstraction," filed Feb. 26, 2002.

At step 760, a query against the queryable database is received and executed. More specifically, a query against one or more tables of the queryable database is received. The query is configured to identify the one or more objects of the data abstraction model by specifying one or more conditions based on the metadata. Then, a query result identifying the one or more objects that satisfy the one or more conditions is returned. Method 700 then exits at step 770.

An Exemplary User Interface for Querying Dam Metadata

As was noted above, a user may use a suitable user interface for creating queries against the queryable database (e.g., data structure 430 of FIG. 4). An exemplary user interface 810 which allows user specification of such queries is described below with reference to FIGS. 8A-B. By way of example, FIGS. 8A-B illustrate an embodiment, where the exemplary user interface 810 is configured for user specification of an query against a metadata abstraction model, for example, to identify logical fields of interest for use in constructing an abstract query.

Figures 8A, 8B:
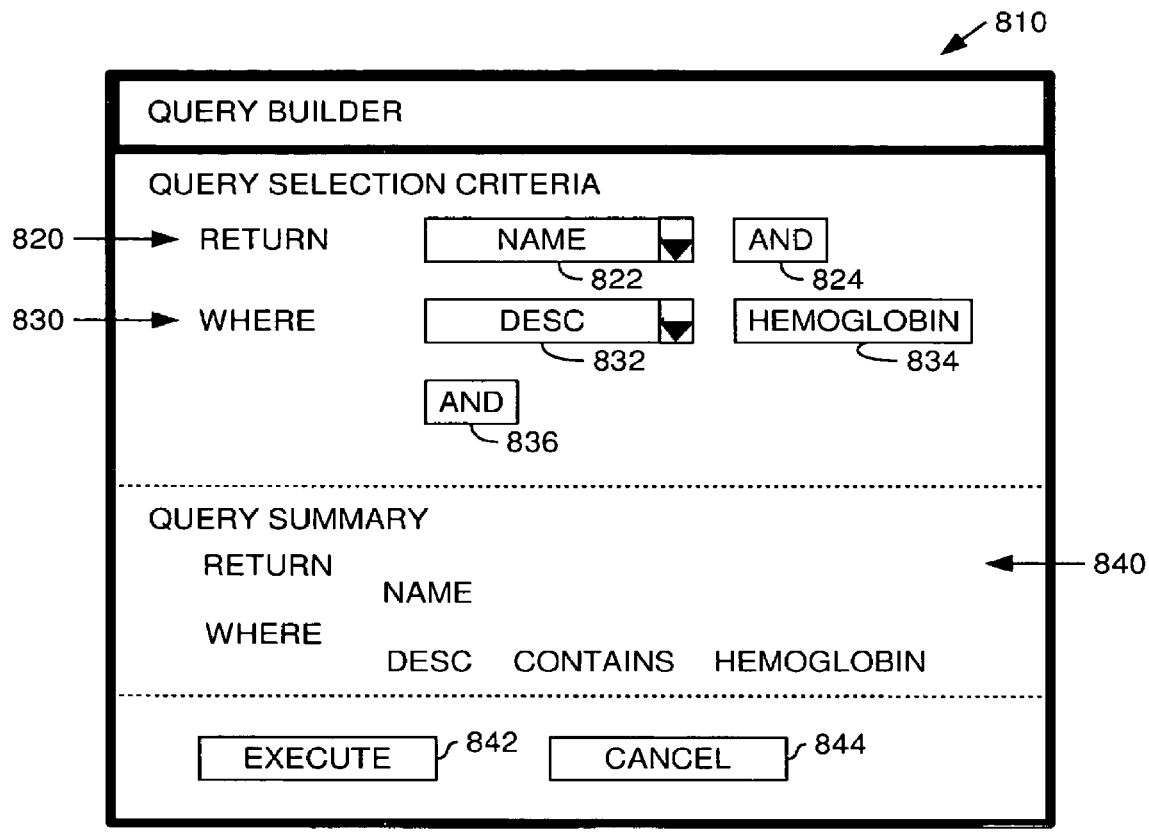
FIGS. 8A-B are user interfaces configured for specification of objects in a data abstraction model in one embodiment.

Referring now to FIG. 8A, the exemplary user interface 810 is shown in an operation for query specification. The user interface 810 displays a result field selection area 820 and a selection criteria selection area 830. Illustratively, each of the result field selection area 820 and the selection criteria selection area 830 displays a plurality of graphical selection elements.

The result field selection area 820 allows for selection of result fields, i.e., objects to be retrieved from an underlying data abstraction model using the metadata abstraction model. To this end, the result field selection area 820 displays a drop-down list 822 which allows the user to select an object of the underlying data abstraction model which should be identified. The drop-down list 822 can be dropped down to display a list of available objects. More specifically, the drop-down list 822 can be dropped down to display a list of fields/columns in a corresponding node table (e.g., node table 602 of FIG. 6A). For instance, the user may position a cursor over an indication of a node "NAME" in the drop-down list 820 and clicks the left mouse button to select this table. The result field selection area 820 further displays a pushbutton 824 "AND" which allows specification of more than one result field using the drop-down list 822, whereby all selected result fields are logically combined in a corresponding query using a Boolean "AND" operator.

The selection criteria selection area 830 allows for selection of selection criteria, i.e., query conditions for the query. To this end, the selection criteria selection area 830 displays a drop-down list 832 which allows the user to select a column of an underlying field table (e.g., field table 606 of FIG. 6B) and/or an underlying category table (e.g., category table 604 of FIG. 6C), on which a condition might be build. Accordingly, the drop-down list 832 can be dropped down to display a list of all columns contained in the underlying field and category tables. The user may position a cursor over an indication of a column "DESC" (e.g., column 639 of FIG. 6B and column 654 of FIG. 6C) in the drop-down list 832 and clicks the left mouse button to select this column. The selection criteria selection area 830 further displays a text field 834 which allows the user to indicate one or more key words that should be searched in the selected column. Illustratively, the user uses the computer mouse to position a cursor over the text field 834, selects the text field 834 using the computer mouse and enters the key word "Hemoglobin". Moreover, the selection criteria selection area 830 displays a pushbutton 836 "AND" which allows specification of more than one query condition using the drop-down lists 832 and 834, whereby all specified query conditions are logically combined in a corresponding query using a Boolean "AND" operator.

The user interface 810 further includes an exemplary query summary display area 840 which displays a query summary on the basis of all selections/specifications which are performed using the result field selection area 820 and the selection criteria selection area 830. Upon specification of a given query, the user may click a pushbutton "EXECUTE" 842 to execute the query against the metadata abstraction model or a pushbutton "CANCEL" 844 to disregard the specification of the query. Assume now that the user has clicked on the pushbutton "EXECUTE" 842. Accordingly, the specified query displayed in the query summary display area 840 is executed against the metadata abstraction model. The user interface 810 then displays a query result, as illustrated in FIG. 8B.

An illustrative query as an example for the specified query is shown in Table III below. For brevity and simplicity, the illustrative query is defined as a worded request for retrieving names "NAME" of logical fields and categories in the underlying data abstraction model, which include a description "DESC" containing the key word "Hemoglobin".

TABLE III

| QUERY EXAMPLE | |
|---|---|
| 001 | RETURN |
| 002 | Name |
| 003 | WHERE |
| 004 | DESC contains Hemoglobin |

Referring now to FIG. 8B, the user interface 810 displays an exemplary query result 850. By way of example, the exemplary query result 850 is presented in tabular form and includes a plurality of columns 852, 856 and 854 and a plurality of rows 862, 864 and 866. Each of the rows 862, 864 and 866 refers to an object of the underlying data abstraction model which has been identified in response to the specified query of FIG. 8A. Column 852 includes information about the selected result field "Name". Column 854 includes for each row the descriptive text included in the "DESC" column which contains the key word "Hemoglobin". Column 856 indicates whether a given row refers to a logical field (F) or a category (C) of logical fields in the underlying data abstraction model. It should be noted that columns 856 and 866 have been displayed for purposes of illustration only. It should be noted that selection of these columns was not illustrated in FIG. 8A described above.

It should be noted that any reference herein to particular values, definitions, programming languages and examples is merely for purposes of illustration. Accordingly, the invention is not limited by any particular illustrations and examples. Furthermore, while the foregoing is directed to embodiments of the present invention, other and further embodiments of the invention may be devised without departing from the basic scope thereof, and the scope thereof is determined by the claims that follow.

What is claimed is:

1. A non-transitory computer-readable storage medium containing a program which, when executed by a processor, performs operations for generating metadata describing objects of a data abstraction model with logical fields that define abstract views of physical data in a database, the operations comprising:
    traversing a logical tree structure representing the data abstraction model, the logical tree structure having a plurality of nodes;
    determining a node type for each node of the plurality of nodes, wherein the node type specifies whether the node is a logical field and a category;
    identifying metadata from the data abstraction model describing the plurality of nodes;
    storing, for each node of the plurality of nodes, the node type and the identified metadata in a queryable database; and
    processing a query issued against the queryable database to identify objects in the data abstraction model available to be used to construct an abstract query;
    wherein storing the identified metadata in a queryable database comprises:
    creating a first database table configured to allow unique identification of each node contained in the logical tree structure; and
    creating a second database table configured to provide detail information for at least a portion of the nodes identified in the first database table.

2. The non-transitory computer-readable storage medium of claim 1, wherein the second database table is configured to provide detail information for each node identified in the first database table and being associated with a logical field of the data abstraction model.

3. The non-transitory computer-readable storage medium of claim 2, wherein each node representing a category of logical fields is a parent node and is defined by a category specification of the data abstraction model; and further comprising identifying metadata contained in the category specification; and wherein storing includes storing the identified metadata contained in the category specification.

4. The non-transitory computer-readable storage medium of claim 3, further comprising creating a third database table configured to provide detail information for each node identified in the first database table and being associated with a category specification.

5. The non-transitory computer-readable storage medium of claim 4, wherein creating the first database table comprises: creating a row for each node contained in the logical tree structure, each row containing a field entry for at least: (i) the node type of the respective; (ii) an identifier of the respective node; and (iii) left and right indicators used to delineate nested set hierarchy notation between nodes corresponding to different rows in the first database table.

6. The non-transitory computer-readable medium storage of claim 4, wherein a combination of the node type and the identifier forms a unique identifier of the respective node.

7. A non-transitory computer-readable storage medium containing a program which, when executed by a processor, performs operations for generating metadata describing objects of a data abstraction model with logical fields that define abstract views of physical data in a database, the operations comprising:
    traversing a logical tree structure representing the data abstraction model, the logical tree structure having a plurality of nodes;
    determining a node type for each node of the plurality of nodes, wherein the node type specifies whether the node is a logical field and a category;
    identifying metadata from the data abstraction model describing the plurality of nodes;
    storing, for each node of the plurality of nodes, the node type and the identified metadata in a queryable database; and
    processing a query issued against the queryable database to identify objects in the data abstraction model available to be used to construct an abstract query;
    wherein:
    traversing the logical tree structure comprises traversing the logical tree structure according to a standard prefix traversal; and
    the identified metadata comprises standard prefix information for corresponding nodes.

8. A non-transitory computer-readable storage medium containing a program which, when executed by a processor, performs operations for identifying an object in a data abstraction model defining an abstract view of physical data in a database, the operations comprising:
    providing the data abstraction model, wherein the data abstraction model includes a plurality of objects comprising one or more category specifications and a plurality of logical fields, each logical field defining an abstract view of a specific set of the physical data;
    receiving a query against one or more database tables containing metadata describing at least some of the plurality of objects, the query configured to identify one or more of the objects by specifying one or more conditions based on the metadata;
    executing the query, by a processor, to produce a query result identifying one or more of the objects that satisfy the one or more conditions, comprising:
    accessing a first database table configured to allow unique identification of each logical field and each category specification contained in the data abstraction model;
    for each of the one or more objects, determining whether the object is a logical field or a category specification;
    for each object being a logical field:
    accessing a second database table configured to provide detail information for each logical field of the data abstraction model; and
    retrieving detail information for the object; and
    for each object being a category specification:
    accessing a third database table configured to provide detail information for each category specification of the data abstraction model; and
    retrieving detail information for the object; and
    wherein the retrieved detail information defines the query result; and
    returning the query result.

9. The non-transitory computer-readable storage medium of claim 8, wherein the first database table comprises:
   a row for each object contained in the data abstraction model, each row containing a field entry for at least:
   (i) a node type indicating whether the respective object represents a logical field or a category specification;
   (ii) an identifier of the respective object; and
   (iii) left and right indicators used to delineate nested set hierarchy notation between objects corresponding to different rows in the first database table.

10. A system, comprising:
   a processor communicatively coupled to a storage medium;
   a database;
   a data abstraction model defining an abstract view of physical data in the database and including a plurality of objects comprising one or more category specifications and a plurality of logical fields, each logical field defining an abstract view of a specific set of the physical data;
   one or more database tables containing metadata describing at least some of the plurality of objects, wherein the database tables are resident on the storage medium; and
   a data abstraction model metadata manager configured to:
      receive a query against the one or more database tables, the query configured to identify one or more of the objects by specifying one or more conditions based on the metadata;
      execute the query to produce a query result identifying one or more of the objects that satisfy the one or more conditions, comprising:
      accessing a first database table configured to allow unique identification of each logical field and each category specification contained in the data abstraction model;
      for each of the one or more objects, determining whether the object is a logical field or a category specification;
      for each object being a logical field:
      accessing a second database table configured to provide detail information for each logical field of the data abstraction model; and
      retrieving detail information for the object; and
      for each object being a category specification:
      accessing a third database table configured to provide detail information for each category specification of the data abstraction model; and
      retrieving detail information for the object; and
      wherein the retrieved detail information defines the query result; and
   return the query result.

* * * * *